United States Patent
Ruider et al.

(10) Patent No.: US 6,323,371 B2
(45) Date of Patent: Nov. 27, 2001

(54) PROCESS FOR THE PREPARATION OF ALKANOLAMINES HAVING IMPROVED COLOR QUALITY

(75) Inventors: Günther Ruider, Wachenheim; Karl-Heinz Ross, Grünstadt; Johann-Peter Melder, Böhl-Iggelheim; Gerhard Schulz, Ludwigshafen, all of (DE); Frank Gutschoven, Antwerpen; Philip Buskens, Hoogstraten, both of (BE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/805,725

(22) Filed: Mar. 7, 2001

(30) Foreign Application Priority Data

Mar. 11, 2000 (DE) ............................................. 100 11 942

(51) Int. Cl.⁷ ................................................. C07C 209/84
(52) U.S. Cl. ........................................... 564/497; 564/498
(58) Field of Search ...................................... 564/497, 498

(56) References Cited

U.S. PATENT DOCUMENTS

| 3,207,790 | 9/1965 | Glew . |
| 4,567,303 | 1/1986 | Boettger . |
| 5,331,102 | * 7/1994 | Gibson ................................. 564/498 |
| 5,693,866 | * 12/1997 | Roling et al. ........................ 564/497 |
| 5,847,221 | * 12/1998 | Gibson ................................. 564/498 |

FOREIGN PATENT DOCUMENTS

| 004 015 | 9/1979 | (EP) . |
| 036 152 | 9/1981 | (EP) . |
| 00/32553 | 6/2000 | (WO) . |

OTHER PUBLICATIONS

SRI Int.,Report No. 193, 1/91,by Process Economics Program.
Thermal Transformation of Ethanolamines, Smirnova et (1991).
DerwentAbstr.No. 76608V44,Chem.Abstr.82:3766h (1974).
GermanPat.Appl., 19942300.8, Apr. 9, 1999.
Derwent Abstr.No.92–393250/48,Chem.118:101513e (1992) al., UDS 547.435.1:543.88. 1989, Plenum Pub.Corp.
Chem.&Eng.News,1996,9/16, Seite 42,Mittlere Spalte.

* cited by examiner

*Primary Examiner*—Johann Richter
*Assistant Examiner*—Brian J. Davis
(74) *Attorney, Agent, or Firm*—Keil & Weinkauf

(57) ABSTRACT

Preparation of alkanolamines having improved color quality by treating the alkanolamine with an effective amount of phosphorous acid or hypophosphorous acid or compounds thereof initially at elevated temperature over a period of at least 5 min (step a), and then distilling it in the presence of an effective amount of one of these phosphorus compounds (step b).

9 Claims, No Drawings

PROCESS FOR THE PREPARATION OF ALKANOLAMINES HAVING IMPROVED COLOR QUALITY

The present invention relates to a process for the preparation of alkanolamines having improved color quality.

Important fields of use of alkanolamines, such as, for example, triethanolamine (TEA), or secondary products thereof, are, for example, soaps, cleansers and shampoos in the cosmetics industry, and also dispersants and emulsifiers.

For these and other fields of use, water-clear, colorless alkanolamines having as little discoloration as possible, e.g. measured as APHA or Gardner color number, which retain these properties even over relatively long storage periods (of, for example, 6, 12 or more months) are desired.

A known problem is that a pure alkanolamine obtained following fractional distillation of an alkanolamine crude product which has been obtained, for example, by reacting ammonia with ethylene oxide or propylene oxide has a yellowish to brownish discoloration (color number e.g. about 10 to 500 APHA in accordance with DIN ISO 6271 (=Hazen)). This discoloration arises particularly in processes involving high temperatures.

During storage of the alkanolamine, including in sealed packs or with the exclusion of light, this discoloration is further intensified. (See e.g.: T. I. MacMillan, Ethylene Oxide Derivatives, Report No. 193, chapter 6, pages 6-5 and 6-9 to 6-13, 1991, SRI International, Menlo Park, Calif. 94025; G. G. Smirnova et al., J. of Applied Chemistry of the USSR 61, pp. 1508–9 (1988), and Chemical & Engineering News, Sep. 16, 1996, page 42, middle column).

A number of processes for the preparation of alkanolamines having improved color quality are described in the literature.

EP-A-36 152 and EP-A-4015 describe the effect of the materials used in processes for the preparation of alkanolamines on the color quality of the process products and recommend nickel-free or low-nickel steels.

U.S. Pat. No. 3,207,790 describes a process for improving the color quality of alkanolamines by the addition of a borohydride of an alkali metal to the alkanolamine.

However, the presence of an auxiliary (stabilizer) for improving the color quality of alkanolamines is undesirable in many important areas of application.

The earlier German Application No. 19942300.8 from 04.09.99 relates to a process for the preparation of alkanolamines having improved color quality by treating the alkanolamine with hydrogen in the presence of a hydrogenation catalyst at elevated temperature.

JP-A-04 29 0850 (Derwent Abstract No. 92-393250/48; Chem. Abstr. 118: 101513e) describes the decoloration of triethylenetetramine by heating in the presence of phosphorous acid and water.

JP-A-49 07 6804 (Derwent Abstract No. 76608V 44; Chem. Abstr. 82:3766h) relates to the purification of ethyleneamines, such as triethylenetetramine or pentaethylenehexamine by distillation in the presence of esters of phosphorous acid.

EP-A-4015 describes how mono-, di- and triethanolamine having reduced discoloration are obtained by the addition of phosphorous or hypophosphorous acid or derivatives thereof before, during or directly after the stepwise reaction of ethylene oxide with ammonia and subsequent isolation by distillation. Page 2, lines 14 to 18 teach that it is not possible to decolorize to a satisfactory degree ethanolamines which already have a greater or lesser degree of discoloration by a distillation carried out in the presence of phosphorous acid. EP-A-4015 teaches that it is instead necessary for the phosphorous or hypophosphorous acid to be present during the preparation of the ethanolamine or at least be added to the crude reaction mixture comprising the ethanolamines, water and ammonia directly after the reaction (cf. the examples and the patent claim).

The earlier German Application No. 19855383.8 from 01.12.98 relates to a process for the purification of TEA prepared by reacting aqueous ammonia with ethylene oxide in liquid phase under pressure and at elevated temperature by separating off excess ammonia, water and monoethanolamine from the reaction product, reacting the resulting crude product with ethylene oxide at temperatures of from 110 to 180° C., and then rectifying the mixture in the presence of phosphorous or hypophosphorous acid or compounds thereof.

It is an object of the present invention to find an economic, selective, efficient and technically noncomplex process for the preparation of alkanolamines having improved color quality. The process should, by overcoming the disadvantages of the prior art, permit the discoloration of alkanolamines (such as, for example, triethanolamine or aminoethylethanolamine), e.g. measured as APHA color number, to be reduced and the color stability to be improved (undesired increase in color number over the storage period).

We have found that this object is achieved by a process for the preparation of alkanolamines having improved color quality, which comprises treating the alkanolamine with an effective amount of phosphorous acid or hypophosphorous acid or compounds thereof initially at elevated temperature over a period of at least 5 min (step a), and then distilling it in the presence of an effective amount of one of these phosphorus compounds (step b).

The alkanolamine used in the process according to the invention, preferably ethanolamine or propanolamine, can be obtained by known processes, e.g. by the reaction of ammonia or of a primary or secondary amine with ethylene oxide or propylene oxide (e.g. as in EP-A-673 920), by the 1,4-addition of ammonia or of a primary or secondary amine to an $\alpha,\beta$-unsaturated aldehyde (e.g. acrolein) and subsequent reduction (e.g. hydrogenation), by the 1,4-addition of ammonia or of a primary or secondary amine to an $\alpha,\beta$-unsaturated acid (e.g. acrylic acid) or an $\alpha,\beta$-unsaturated ester (e.g. acrylic ester) and subsequent reduction (e.g. hydrogenation), by the 1,4-addition of water to an $\alpha,\beta$-unsaturated nitrile (e.g. acrylonitrile) and subsequent reduction (e.g. hydrogenation), amination of corresponding primary or secondary alcohols, or aminating hydrogenation of corresponding hydroxyaldehydes or hydroxyketones.

N-(2-Aminoethyl)ethanolamine (AEEA) can be obtained by the reaction of monoethanolamine or ammonia with ethylene oxide in the presence of hydrogen and a hydrogenating, dehydrogenating or aminating catalyst.

The purity of the alkanolamines used in the process according to the invention, preferably ethanolamines or propanolamines, is generally greater than 70% by weight, in particular greater than 80% by weight. As well as distilled or undistilled crude alkanolamines, which can also be removed directly in crude form from the corresponding precursors from a plant for the preparation of the alkanolamine, it is also possible to use distilled alkanolamines having a purity of greater than 90% by weight, particularly $\geq 97\%$ by weight, in particular $\geq 98\%$ by weight, very particularly $\geq 99\%$ by weight.

It is also possible to use mixtures of alkanolamines, in which case the purities given above are based on each alkanolamine of this mixture, or solutions of alkanolamines in an inert solvent, such as, for example, alcohols (methanol, ethanol, isopropanol, n-propanol, n-butanol, 2-ethylhexanol), ethers (tetrahydrofuran, 1,4-dioxane), hydrocarbons (benzene, pentane, petroleum ether, toluene, xylene, hexane, heptane, Mihagol) and water.

The APHA color number of the alkanolamines used (based on the non-acid-treated alkanolamine) is generally $\leq 100$, in particular $\leq 50$, for example $\leq 20$.

The alkanolamines which are preferably used in the process according to the invention are ethanolamines and propanolamines such as, for example, monoethanolamine (MEA), diethanolamine (DEA), triethanolamine (TEA), O,N,N-tris(2-hydroxyethyl)ethanolamine, N-(2-aminoethyl) ethanolamine (AEEA), N-(2-hydroxyethyl)piperazine, N-(2-hydroxyethyl)morpholine, N,N'-bis(2-hydroxyethyl) piperazine, monoisopropanolamine, diisopropanolamine, triisopropanolamine and 1,3-propanolamine, particularly preferably the ethanolamines MEA, DEA, TEA and AEEA.

The process according to the invention can be carried out as follows:

In a first process step (step a), the alkanolamine whose color quality is to be improved, or a mixture of the alkanolamines in liquid phase, optionally in the presence of an inert solvent, in a suitable (stirred) container, which may be fitted with a reflux condenser, is treated with an effective amount of phosphorous acid ($H_3PO_3$), hypophosphorous acid ($H_3PO_2$) or compounds of these acids, advantageously with stirring or recirculation, and the mixture is heated over a period of generally at least 1 minute, particularly at least 5 min, in particular at least 10 min (for example 10 min to 50 hours, in particular 10 min to 24 hours), very particularly at least 15 min (for example 15 min to 2 hours), particularly preferably at least 30 min (for example 30 min to 2 hours), at temperatures of from 40 to 250° C., in particular 100 to 250° C., very particularly 120 to 220° C., particularly preferably 150 to 220° C.

For better handlability, it may be advantageous to meter in the effective amount of phosphorous acid, hypophosphorous acid or compounds of these acids in a suitable inert diluent or solvent, such as, for example, water, alcohols (methanol, ethanol, isopropanol, n-propanol), ethers (tetrahydrofuran, 1,4-dioxane) or an alkanolamine (e.g. an ethanolamine, such as onoethanolamine, diethanolamine, triethanolamine, N-(2-aminoethyl)ethanolamine), where the alkanolamine can here also be the same as the alkanolamine process product, in the form of a solution or suspension.

The required treatment time of the alkanolamine (or of the mixture of the alkanolamines) with the phosphorus compound is determined inter alia from the degree of discoloration of the alkanolamine used and the extent of desired decoloration and/or color stability of the alkanolamine. As a rule, for a given temperature, the higher the degree of decoloration of the alkanolamine used in the process according to the invention and the higher the requirements on the color quality of the process product, the longer the treatment time.

The temperature must not, however, be chosen to be too high, i.e. as a rule no greater than 250° C., since otherwise acid-induced degradation of the alkanolamine occurs, which has a negative effect on the color quality of the alkanolamine ultimately obtained.

The most favorable temperatures and treatment times for the alkanolamine in question can be readily determined in simple preliminary experiments.

During this treatment of the alkanolamine with the phosphorus compound, it is advantageous if the mixture is further stirred throughout the entire treatment period or occasionally (e.g. stirred or recirculated).

It is also advantageous if the treatment of the alkanolamine is carried out under a protective-gas atmosphere (e.g. $N_2$ or Ar).

The treatment of the alkanolamine with the phosphorus compound can also be carried out continuously in suitable containers, e.g. in a tubular reactor or in a cascade of stirred containers.

The treatment of the alkanolamine can advantageously be carried out in the still container of a distillation column or in a distillation receiver vessel.

In one particular embodiment of this first process step, during the treatment of the alkanolamine, an inert gas (e.g. $N_2$ or Ar) is passed as stripping stream through the alkanolamine in order to remove from the mixture low-boiling components which form and which may have a negative effect on the color quality, such as, for example, acetaldehyde or secondary products thereof.

In another particular embodiment of this first process step, the alkanolamine to be treated is circulated in liquid form via a heat exchanger, and low-boiling components which form, which may have a negative effect on the color quality, such as, for example, acetaldehyde, are drawn off in the process.

The heat exchanger here can be an open heat exchanger such as, for example, a falling-film evaporator or wiper-blade evaporator, or a sealed heat exchanger, such as, for example, a plate-type heat exchanger or shell-and-tube heat exchanger.

Depending on the reaction conditions chosen, it may be necessary to carry out the treatment of the alkanolamine at superatmospheric pressure (e.g. 0.1 to 50 bar) in order to avoid the undesired escape of one or more components from the mixture.

The phosphorous acid or hypophosphorous acid can be used in the process according to the invention in monomeric or else in polymeric form, in hydrous form (hydrates) or as an addition compound (e.g. on an inorganic or organic support such as $SiO_2$, $Al_2O_3$, $TiO_2$, $ZrO_2$).

Suitable for the process according to the invention are also compounds of phosphorous or hypophosphorous acid, such as salts (e.g. disodium hydrogenphosphite ($Na_2HPO_3$), disodium hydrogenhypophosphite ($Na_2HPO_2$)), dipotassium hydrogenphosphite ($K_2HPO_3$), diammonium hydrogenphosphite (($NH_4)_2HPO_3$)), amides, esters (e.g. triethyl phosphite or triphenyl phosphite) or anhydrides thereof (e.g. $P_2O_3$) or mixtures of the abovementioned phosphorus compounds.

Here, the salts can either be used directly as such, or be obtained by mixing, either in situ or prior to use in the treatment, a basic, organic or inorganic salt, such as NaOH, KOH, Ca(OH)$_2$, NH$_4$OH, Na$_2$CO$_3$, K$_2$CO$_3$, NaOMe or NaOEt, optionally in a suitable solvent, with the phosphorous acid or hypophosphorous acid.

Preference is given to phosphorous acid ($H_3PO_3$), hypophosphorous acid ($H_3PO_2$), disodium hydrogenphosphite ($Na_2HPO_3$), triethyl phosphite, triphenyl phosphite and disodium hydrogenhypophosphite ($Na_2HPO_2$).

The amount of phosphorus compounds added is usually at least 0.01% by weight, preferably 0.01 to 2% by weight, particularly preferably 0.02 to 1.0% by weight, very particularly preferably 0.02 to 0.5% by weight, based on the amount of alkanolamine used, although the effect also occurs if the amounts are larger.

If the phosphorus compounds added are acidic, i.e. have a $pK_a$ value of less than 4, the amount is generally 0.01 to 0.5% by weight (based on the amount of alkanolamine used) in order to largely avoid the induction of acid-catalyzed decomposition reactions of the alkanolamine.

Following the above-described treatment of the alkanolamine (or the mixture of the alkanolamines), the alkanolamine (or the mixture of the alkanolamines) is distilled or rectified in a second process step (step b) in the presence of an effective amount of one or more of the abovementioned phosphorus compounds at reduced pressure.

The amounts of phosphorus compounds in this second process step are in the same range as in the first process step.

In a particular embodiment process, the distillation or rectification of the alkanolamine takes place in the presence of the phosphorus compound or phosphorus compounds already added in the first process step.

The distillation or rectification of the alkanolamine is carried out discontinuously or continuously at a pressure of, as a rule, less than 100 mbar (100 hPa), for example at about 10 to 50 mbar, and at still temperatures of, generally, from 100 to 250° C., where, in the case of the continuous procedure, in a particular embodiment, low-boiling fractions which may be present are drawn off overhead, and the alkanolamine is obtained in a sidestream takeoff.

Some or all of the residue from the distillation or rectification which comprises the added phosphorus compound or reaction products thereof can, in a particular embodiment, be returned to the process.

The process according to the invention produces an alkanolamine having improved color quality which, directly after it has been obtained, has an APHA color number of from 0 to 30, in particular from 0 to 20, very particularly from 0 to 10, and which, after acid treatment, which is carried out as described below under 2a) within 0.5 to 3 hours aft it has been obtained, has an APHA color number of from 0 to 100, in particular from 0 to 60, very particularly from 0 to 40, and an absolute value for the numerical measure a* according to the CIE Lab system of from 0 to 4, in particular from 0 to 3, very particularly from 0 to 2.5, and an absolute value for the numerical measure b* according to the CIE Lab system of from 0 to 8, in particular from 0 to 5, very particularly from 0 to 4, or which, after acid treatment, which is carried out as described below under 2b) within 0.5 to 3 hours after it has been obtained, has a Gardner color number of from 0 to 3, in particular from 0 to 2.5, very particularly from 0 to 2.

EXAMPLES

Preliminary Remarks

1a) Heat Treatment and Distillation (Examples 1 to 11)

The crude triethanolamine (TEA) used in Examples 1 to 11 consisted of a technical-grade stream from the preparation of ethanolamine, consisting of 71% by weight of triethanolamine, 27% by weight of diethanolamine and 2% by weight of other substances (predominantly O,N,N-tris(2-hydroxyethyl)ethanolamine, O,N-bis(2-hydroxyethyl) ethanolamine and bishydroxyethylpiperazine).

A sample of the crude TEA as described above and used in Examples 1 to 11 had, following an industrial distillation, a purity of >99% by weight and, after acid treatment as in 2a) and subsequent measurement as in 2c) in a LICO 200 instrument, values between 4 and 5 both for a* and for b*.

The heat treatment (=process step a) was carried out by heating the crude ethanolamine mixture in a distillation receiver vessel in the presence of the phosphorus compound listed in Table 1 at atmospheric pressure (temperature and duration see Table 1).

Subsequent distillation of the crude triethanolamine in the presence of the phosphorus compound (=process step b) was carried out on a 1 l scale discontinuously at 0.4 to 1.0 mbar using a single-stage laboratory bridge, the still temperature being maintained throughout between 160 and 190° C. and the head temperature between 140 and 170° C.

During the distillation, the distillate was collected in four equal fractions, the first of which typically consisted of approximately 66% by weight of DEA and 33% by weight of TEA, the second of which consisted of 38% by weight of DEA and 61% by weight of TEA, and the third and fourth of which each consisted of >97% by weight of TEA. Since the first two fractions did not comprise representative TEA, they were discarded and not taken into consideration for the color number measurement.

1b) Heat Treatment and Distillation (Examples 12 to 23)

The phosphorus compound given in Table 2 was dissolved, with stirring for approximately 12 hours and where necessary slight warming (max. 40 to 60° C.), in pure AEEA (purity >99% by weight of AEEA; impurities: diethylenetriamine (DETA) and hydroxyethylpiperazine (HEP); color quality: Gardner color number after acid treatment as described under 2b): 6.0, Gardner color number after thermal treatment as described under 2d) and subsequent acid treatment as described under 2b): 6.0).

The feed material prepared in this way and kept under a blanket of nitrogen was pumped through a pipe coil (volume: 50 ml) thermostated in an oil bath, the residence time, amount of additive and temperature being varied as given in Table 2 (=process step a).

The discharge from the pipe coil was passed to a wiper-film evaporator operated at a pressure of 50 mbar and an oil temperature between 150 and 170° C., meaning that a sufficiently high still discharge (about 10 to 20% of the volume stream) was retained in order to avoid deposits on the heating surface. At the top of the wiper-film evaporator, the vaporous AEEA was stripped off and obtained as distillate in a condenser (process step b). To improve separation, a nitrogen stripping stream of 1 l of $N_2$/h was passed upward from below through the wiper-film evaporator.

1c) Heat Treatment and Distillation (Examples 24 to 32)

The phosphorus compound ($H_3PO_3$ or $H_3PO_2$) given in Table 3 was dissolved, with stirring for approximately 12 hours, in pure AEEA (purity >99% by weight of AEEA; impurities: diethylenetriamine (DETA) and hydroxyethylpiperazine (HEP); color quality: Gardner color number after acid treatment as described under 2b): 4.6).

The other process steps were carried out as described under 1b).

2. Determination of the Color Quality of the Alkanolamines

2a) Acid Treatment of the Alkanolamines (Examples 1 to 11)

To amplify the color effects which occur, 20 ml of the alkanolamine sample to be investigated were treated with 1000 ppm of glacial acetic acid and carefully mixed. The mixture was thoroughly stirred and transferred to a test tube, which was left for 3 h in an oil bath thermostated at 100° C. Here, the vessel was sealed with a stopper and kept under nitrogen. The stopper was pierced by a cannula in order to ensure pressure compensation. After 3 h, the vessel was cooled in an ice bath, and directly afterward the color number was measured (see 2c).

2b) Acid Treatment of the Alkanolamines (Examples 12 to 23 and Examples 24 to 32)

10 g of the alkanolamine (e.g. aminoethylethanolamine (AEEA)) were weighed into a 100 ml Erlenmeyer flask and, with stirring (magnetic stirrer) and cooling (ice bath), 12.5 g of 32% strength aqueous hydrochloric acid were introduced over the course of one minute in three portions, initially dropwise, then more quickly, the solution heating up (max. about 30° C.). After a post-cooling period of 2 minutes, a sample of the solution was transferred to a test tube and sealed with a rubber stopper pierced by a cannula. The test tube was heated in a heating bath at 70° C. for one hour. The test tube was then cooled in an ice bath, the ingredients were immediately transferred to a cuvette and the color number was measured (see 2c).

[An acid treatment of an alkanolamine for intensifying color effects has been described generally in JP-A-62 019 558 (Derwent Abstract No. 87-067647/10) and JP-A-62 005 939 (Derwent Abstract No. 87-047397/07), according to which TEA is treated (neutralized) with acetic acid, citric acid, sulfuric acid, hydrochloric acid or phosphoric acid.]

2c) Color Number Measurement (Examples 1 to 32)

In general, the color number of the previously acid-treated sample was measured at a max. of 3 h after cooling in order to keep post-coloration following acid treatment (as a result of aging) as low as possible.

In a spectral color measurement, the values for the numerical measures a* and b* in accordance with the CIE Lab system (according to Judd and Hunter (CIE=Comission International d'Eclairage, Paris); (cf. DIN 6174)), the APHA value (corresponding to DIN-ISO 6271) and the Gardner color number (DIN ISO 4630) were determined.

The a*, b* and APHA values (APHA color number= Hazen color number=Pt/Co color number) in Examples 1 to 11 were determined in the standard manner in a LICO 200 instrument from Dr. Lange in a 5 cm (path length) curette (volume≈10 ml).

The Gardner and APHA values in Examples 12 to 32 were determined in the standard manner in an LTM1 Liquid Tester from Dr. Lange in an 11 mm (internal diameter) round curette.

The a* value gives the red/green coloration of the sample (a positive a* value gives the red color content, and a negative a* value the green color content) and the b* value gives the yellow/blue content (a positive b* value gives the yellow color content, a negative b* value gives the blue color content). A particularly desirable result is an absolute a* value which is lower than that in the starting material prior to carrying out the process according to the invention.

The a*, b*, Gardner and APHA values given in Tables Nos. 1, 2 and 3 refer in every case to the samples after acid treatment carried out in the appropriate manner.

2d) Storage Experiments (Examples 12 to 23)

In order to investigate the color stability of AEEA, 50 g of the AEEA obtained at the distillation were heated at an internal temperature of 90° C. for 3 hours under nitrogen in a three-necked flask with attached water condenser. After cooling to room temperature, the mixture was acid-treated as described above under 2b), and the color number was measured as described above under 2c). This thermal treatment of the AEEA at 90° C. for 3 h simulated storage over about 40 days at 20° C.

Results

The results of Example Nos. 1 to 11, 12 to 23 and 24 to 32 are given in Tables 1, 2 and 3.

Examples 1 to 4, 12, 24 to 27 and 30 are comparative examples.

Example 1 represents distillation of the TEA crude mixture without prior heat treatment as comparative value, whereas Example 2 is with heat treatment (60 min, 180° C.), but in each case without the addition according to the invention of the phosphorus compound.

In both cases, the a* and b* absolute value of the product is unacceptably high.

By adding $H_3PO_3$ or $Na_2HPO_3$ during the distillation, but without prior heat treatment, the color quality was not sufficiently improved (Examples 3 and 4): the a* and/or b* absolute values remained unacceptably high.

Examples 5 to 11

As a result of prior thermal treatment of the alkanolamine in the presence of the phosphorus compounds described, it is possible to achieve an improvement in the color quality to the required color numbers and a* and b* values. In this connection, $H_3PO_3$ is more effective than $Na_2HPO_3$, lowering both the a* and also the b* absolute values. $Na_2HPO_3$ is more effective in reducing the a* absolute value on its own, but has less influence on the b* value.

Examples 13 to 23

The treatment according to the invention of the AEEA with $H_3PO_3$ in each case significantly improved the color quality (compare with Example 12).

The longer the AEEA was pretreated in the presence of $H_3PO_3$, the more favorable the color number of the process product (Example 14 vs. 13, 17 vs. 16 vs. 15 and 20 vs. 19 vs. 18).

Moreover, as the temperatures in the first process step increase, a positive effect is established (Example 18 vs. 13 and 19 vs. 14).

Furthermore, the amount of $H_3PO_3$ added has a positive effect on the color quality (Example 21 vs. 18 vs. 15, and 22 vs. 19 vs. 16).

If AEEA is heat-treated (=process step a) for too long in the presence of amounts of $H_3PO_3$ which are too great at too high a temperature (Example 23 vs. 22), then an impairment in the color number is observed (acid-induced degradation).

Examples 24 to 32

Example 24 shows, as comparison, the result with regard to the color number of a simple distillation of the AEEA over a Sambay evaporator.

According to Examples 24, 27 and 30, distillation of the AEEA in the presence of the phosphorus compound without prior heat treatment according to the invention (step a) does not lead to an improvement in the color number of the alkanolamine.

Examples 28, 29, 31 and 32 are in accordance with the invention and show the improvement in color quality.

TABLE 1

| Example No. | Additive | Heat treatment (process step a) | | Fraction 3 (of the distillation) | | | Fraction 4 (of the distillation) | | |
|---|---|---|---|---|---|---|---|---|---|
| | | Duration [min] | Temperature [° C.] | a* | b* | APHA | a* | b* | APHA |
| 1 | — | — | — | −9.3 | 65.6 | 530 | −6.1 | 24.6 | 168 |
| 2 | — | 60 | 180 | −10.7 | 71.2 | 567 | −8.8 | 30.5 | 254 |

TABLE 1-continued

| Example No. | Additive | Heat treatment (process step a) Duration [min] | Heat treatment (process step a) Temperature [° C.] | Fraction 3 (of the distillation) a* | Fraction 3 (of the distillation) b* | Fraction 3 (of the distillation) APHA | Fraction 4 (of the distillation) a* | Fraction 4 (of the distillation) b* | Fraction 4 (of the distillation) APHA |
|---|---|---|---|---|---|---|---|---|---|
| 3 | 2500 ppm of $H_3PO_3$ | — | — | 4.3 | 3.0 | 35 | 5.1 | 3.3 | 39 |
| 4 | 2200 ppm of $Na_2HPO_3$ | — | — | 2.4 | 16.3 | 130 | 3.3 | 14.1 | 118 |
| 5 | 2500 ppm of $H_3PO_3$ | 30 | 180 | 1.7 | 1.4 | 15 | 2.0 | 2.2 | 22 |
| 6 | 2500 ppm of $H_3PO_3$ | 60 | 180 | 1.3 | 1.2 | 13 | 1.7 | 1.6 | 17 |
| 7 | 4000 ppm of $H_3PO_3$ | 60 | 180 | 1.0 | 0.9 | 10 | 1.4 | 1.1 | 12 |
| 8 | 4000 ppm of $H_3PO_3$ | 10 | 180 | 2.2 | 2.7 | 26 | 2.1 | 3.0 | 28 |
| 9 | 4000 ppm of $H_3PO_3$ | 60 | 150 | 2.0 | 2.6 | 25 | 2.2 | 2.9 | 28 |
| 10 | 2200 ppm of $Na_2HPO_3$ | 60 | 180 | 0.9 | 6.8 | 54 | 0.4 | 7.3 | 56 |
| 11 | 2000 ppm of $P(OPh)_3$ | 60 | 180 | 1.7 | 3.2 | 29 | 2.1 | 4.6 | 41 |

TABLE 2

| Example No. | Additive | Pipe coil Temp. (° C.) | Pipe coil Res. time (min) | Sambay distillation Temp. (° C.) | Sambay distillation Pressure (mbar) | Color number (after acid treatment) APHA | Color number (after acid treatment) Gardner | After storage Color number (after acid treatment) APHA | After storage Color number (after acid treatment) Gardner |
|---|---|---|---|---|---|---|---|---|---|
| 12 | — | 180 | 30 | 160 | 50 | 714 | 3.7 | 762 | 3.9 |
| 13 | 4000 ppm of $H_3PO_3$ | 150 | 10 | 170 | 50 | 430 | 2.5 | 502 | 2.8 |
| 14 | 4000 ppm of $H_3PO_3$ | 150 | 30 | 160 | 50 | 165 | 1.1 | 312 | 1.9 |
| 15 | 2000 ppm of $H_3PO_3$ | 180 | 10 | 170 | 50 | 198 | 1.2 | 252 | 1.6 |
| 16 | 2000 ppm of $H_3PO_3$ | 180 | 30 | 160 | 50 | 145 | 0.9 | 177 | 1.1 |
| 17 | 2000 ppm of $H_3PO_3$ | 180 | 60 | 153 | 50 | 35 | 0.2 | 75 | 0.4 |
| 18 | 4000 ppm of $H_3PO_3$ | 180 | 10 | 170 | 50 | 100 | 0.7 | 125 | 0.8 |
| 19 | 4000 ppm of $H_3PO_3$ | 180 | 30 | 160 | 50 | 100 | 0.6 | 110 | 0.7 |
| 20 | 4000 ppm of $H_3PO_3$ | 180 | 60 | 153 | 50 | 25 | 0.1 | 46 | 0.3 |
| 21 | 10,000 ppm of $H_3PO_3$ | 180 | 10 | 170 | 50 | 36 | 0.2 | 40 | 0.3 |
| 22 | 10,000 ppm of $H_3PO_3$ | 180 | 30 | 160 | 50 | 14 | 0.2 | 48 | 0.3 |
| 23 | 10,000 ppm of $H_3PO_3$ | 180 | 60 | 153 | 50 | 70 | 0.4 | 101 | 0.6 |

(Res. time = residence time)

TABLE 3

| Example No. | Additive | Pipe coil (step a) Temp. (° C.) | Pipe coil (step a) Res. time (min) | Color numbers after Sambay distillation and acid treatment (HCl) APHA | Color numbers after Sambay distillation and acid treatment (HCl) Gardner |
|---|---|---|---|---|---|
| 24 | — | RT | 30 | 505 | 2.9 |
| 25 | — | 180 | 30 | 578 | 3.3 |
| 26 | — | 180 | 10 | 541 | 3.1 |
| 27 | 4000 ppm of $H_3PO_3$ | RT | 30 | 515 | 2.9 |
| 28 | 4000 ppm of $H_3PO_3$ | 180 | 30 | 131 | 0.5 |
| 29 | 4000 ppm of $H_3PO_3$ | 180 | 10 | 149 | 0.6 |
| 30 | 4000 ppm of $H_3PO_2$*) | RT | 30 | 521 | 3.0 |
| 31 | 4000 ppm of $H_3PO_2$*) | 180 | 30 | 216 | 1.0 |
| 32 | 4000 ppm of $H_3PO_2$*) | 180 | 10 | 464 | 2.6 |

(Res. time = residence time)
(RT = room temperature = 22° C.)
*) as 50% strength aqueous solution

We claim:

1. A process for the preparation of alkanolamines having improved color quality, which comprises treating the alkanolamine with an effective amount of phosphorous acid or hypophosphorous acid or compounds thereof initially at elevated temperature over a period of at least 5 min (step a), and then distilling it in the presence of an effective amount of one of these phosphorus compounds (step b).

2. A process as claimed in claim 1, wherein the phosphorus compounds are disodium hydrogenphosphite ($Na_2HPO_3$), triethyl phosphite, triphenyl phosphite or disodium hydrogenhypophosphite ($Na_2HPO_2$).

3. A process as claimed in claim 1, wherein the alkanolamine is an ethanolamine or propanolamine.

4. A process as claimed in claim 1, wherein the alkanolamine is monoethanolamine, diethanolamine or triethanolamine.

5. A process as claimed in claim 1, wherein the alkanolamine is N-(2-aminoethyl)ethanolamine and the phosphorus compounds are phosphorous acid or hypophosphorous acid.

6. A process as claimed in claim 1, wherein the treatment of the alkanolamine in step a is carried out over a period of from 10 min to 50 hours.

7. A process as claimed in claim 1, wherein the treatment of the alkanolamine in step a is carried out at temperatures of from 40 to 250° C.

8. A process as claimed in claim 1, wherein the treatment of the alkanolamine in step a and the distillation of the alkanolamine (step b) are in each case carried out in the presence of from 0.01 to 2% by weight of the phosphorus compound.

9. A process as claimed in claim 1, wherein the prepared alkanolamine, following treatment for three hours with 1000 ppm of glacial acetic acid at 100° C., has an APHA color number (DIN ISO 6271) of from 0 to 100, an absolute value for the numerical measure a* according to the CIE Lab system of from 0 to 4 and an absolute value for the numerical measure b* according to the CIE Lab system of from 0 to 8, or following treatment for one hour with 1.25 times the amount by weight of 32% strength aqueous hydrochloric acid at 70° C., a Gardner color number (DIN ISO 4630) of from 0 to 3.

* * * * *